United States Patent [19]
Schenck

[11] Patent Number: 5,486,187
[45] Date of Patent: Jan. 23, 1996

[54] ANASTOMOSIS DEVICE AND METHOD

[76] Inventor: Robert R. Schenck, 1100 N. Lake Shore Dr., Chicago, Ill. 60611

[21] Appl. No.: 177,260

[22] Filed: Jan. 4, 1994

[51] Int. Cl.$^6$ ................................................. A61B 17/00
[52] U.S. Cl. ............................................ 606/153; 606/151
[58] Field of Search .................................... 606/151, 153, 606/154, 155, 156; 623/1, 12

[56] References Cited

U.S. PATENT DOCUMENTS

| | | |
|---|---|---|
| 2,453,056 | 11/1948 | Zack . |
| 3,254,651 | 6/1966 | Collito . |
| 3,316,914 | 5/1967 | Collito . |
| 3,774,615 | 11/1973 | Lim et al. . |
| 3,908,662 | 9/1975 | Razgulov et al. . |
| 3,974,835 | 8/1976 | Hardy, Jr. . |
| 4,055,186 | 10/1977 | Leveen . |
| 4,352,358 | 10/1982 | Angelchik . |
| 4,368,736 | 1/1983 | Kaster . |
| 4,470,415 | 9/1984 | Wozniak . |
| 4,474,181 | 10/1984 | Schenck . |
| 4,523,592 | 6/1985 | Daniel . |
| 4,593,693 | 6/1986 | Schenck . |
| 4,624,255 | 11/1986 | Schenck et al. . |
| 4,693,249 | 9/1987 | Schenck et al. . |
| 4,771,775 | 9/1988 | Walsh et al. ............................ 606/153 |
| 4,899,744 | 2/1990 | Fujitsuka et al. ....................... 606/153 |
| 5,188,638 | 2/1993 | Tzakis ..................................... 606/151 |
| 5,234,447 | 8/1993 | Kaster et al. ........................... 606/151 |

FOREIGN PATENT DOCUMENTS

| | | |
|---|---|---|
| 0537757 | 4/1993 | European Pat. Off. . |
| 2101284 | 7/1971 | Germany . |
| 1181563 | 2/1970 | United Kingdom . |

OTHER PUBLICATIONS

Russian reference entitled, "A New Method for a Circular Vascular Suture," by D. A. Donetskii, published 1956, in Eksperim Khrur.1, pp. 53–59, along with an English translation.

Primary Examiner—Stephen C. Pellegrino
Assistant Examiner—Jeffrey A. Schmidt
Attorney, Agent, or Firm—Fitch, Even, Tabin & Flannery

[57] ABSTRACT

In accordance with the present invention, there is provided new and improved apparatuses and methods for anastomosing living vessels. The preferred apparatus includes a ring-like body through which a first living vessel end is extended and everted back over and a second living vessel end which is drawn over the everted first living vessel end to place the lumen of these vessels in apposition. A plurality of fasteners are employed to clinch the vessel ends in sealed apposition at the ring-like body. These preferred fasteners are staple-like and have one leg located inside of the ring-like body but exterior of the first living vessel, and a second leg located exterior of the margin of the second living vessel at the ring-like body. The ring-like body may also be provided with at least one needle-like projection which may be adapted to either permanently impale and hold the vessel ends at the ring-like body or temporarily impale and hold the vessel ends until the fastener are employed. In accordance with the method for employing the apparatuses of the present invention, there is provided a surgeon's tool for holding and controlling the ring-like body and a surgeon's tool for impaling and manipulating the vessel ends to bring them simultaneously into position at the ring-like body. Additionally, a surgeon's tool is provided for closing fasteners in accordance with the present invention. The surgeon's tool is employed to shut the staple-like fasteners to clinch the vessel ends in a sealed apposition at the ring-like body.

6 Claims, 6 Drawing Sheets

ANASTOMOSIS DEVICE AND METHOD

FIELD OF THE INVENTION

The present invention is directed to apparatus and methods for anastomosing ends of living vessels and, more particularly, to sutureless anastomosing apparatus and methods in which encircling members and fasteners are employed for anastomosing living vessel ends.

BACKGROUND OF THE INVENTION

Anastomosis, or joining of severed blood vessels, is among the vital and time consuming tasks associated with surgical procedures. Hence, the success of a given surgical procedure may hinge upon the degree of circulation restored to the interconnected vessels through such anastomosis procedure.

A wide variety of anastomosis devices and methods have been developed for anastomosing ends of living vessels. One known procedure for anastomosing blood vessels includes the use of sutures, i.e., stitches. One known shortcoming with conventional suturing techniques is their tendency to be relatively tedious, particularly with blood vessels of small diameters, such as vessels being one millimeter or less in diameter. Experience has revealed that this is especially the case when anastomosing children's vessels because they are even smaller and prone to spasm. In addition, successful anastomosing of blood vessels is highly dependent on the proper placement of the sutures by the surgeon. Thus, in certain instances, such known conventional suturing anastomosing techniques are time-consuming to a point that undesirable extends the duration of a surgical procedure.

With the exception of the aorta and vena cava, human blood vessels have a naturally occurring contractility known as circumferential compressive stress which resists dilation. As the vessel diameter decreases and the relative wall thickness increases, these compressive forces become proportionately larger. Radial tethering forces of tissues do exist around the vessel, but these are of lesser significance than longitudinal vessel motion tethering. It is therefore important to consider these forces to assure patency, i.e., the vessels ability to conduct blood flow, at the anastomosis site.

Even successful suturing of blood vessels does not assure continued patency at the sutured site. It is known that clotting of blood, known as "thrombosis," may act to block blood flow through an anastomosed vessel. In addition to the already mentioned forces, thrombosis after microvascular repair may be caused by a number of other factors which include inaccurate placement of sutures, vessel spasms, stenosis and microclamp damage. Furthermore, it has been found that continuity of flow during the first twenty minutes after anastomosis is critical in preventing thrombus formation and that platelet aggregation, and later resolution, occurs in the first several hours after a microvascular anastomosis. Hence, it is critical that anastomosing procedures employ effective devices and be performed relatively quickly to relieve the procedure of the above-mentioned shortcomings.

To aid in anastomosing blood vessels, a number of implantable devices have been employed at the anastomosis site for assisting to interconnect severed ends of blood vessels. Such devices, and methods for employing the same, are disclosed in U.S. Pat. Nos. 3,254,650 and 4,055,186, British Patent No. 1,181,563, German Fed. Rep. Patent No. 2,101,282 and Nakayama et al. *Surgery* December 1962, pp. 918–931. Other devices, such as that disclosed in U.S. Pat. No. 2,180,337, have the severed ends of the blood vessels everted over the device to facilitate suturing.

Another known device for aiding in anastomosing blood vessels is disclosed in U.S. Pat. No. 4,474,181. This patent discloses an implantable external ring to which a pair of vessels, having prepared openings, may be tethered with sutures so as to hold their intima in fluid-tight apposition. The ring maintains the lumen of the vessels in an expanded condition at the anastomosis site, which tends to provide assurance of patency. Hence, this device is highly effective for providing patency at the anastomosis site by countering the already mentioned concerns pertaining to thrombosis at the susceptible site, i.e., the anastomosis site.

However, one known shortcoming with suturing the vessel ends at the ring is the difficulty of this procedure, particularly for relatively small vessels, and the time demands. In a typical surgical procedure, a large number of vessels my require anastomosis, in which many of these are relatively small vessels, and the time consumed anastomosing vessels by suturing contributes significantly to the overall time necessary to complete the surgical procedure. It would therefore be desirable and advantageous to reduce the anastomosis time by avoiding the use of sutures altogether.

One known solution attempting to solve the disadvantages associated with suturing at a ring is disclosed in A. D. Donetskii, *Eksperim Khirur* pp. 153–59 (1956). The disclosed device includes an anastomosis ring having radially and outwardly extending protrusions for impaling the vessel ends, and thereby securing them in apposition at the ring. More particularly, the end of the first vessel is initially inserted through the ring opening and then everted around and over the outside surface of the ring and impaled on the radial protrusions, and then, the end of the second vessel is drawn over the everted first vessel end and also impaled on the radial protrusions.

one known shortcoming with simply impaling the vessel ends at the ring with the known radial protrusions is that some of the smaller and weaker vessels tend to tear during the anastomosis procedure. That is, with a ring having three radially and outwardly extending protrusions, the vessel ends tend to tear while the vessel is being stretched to be impaled on the third protrusion after first being impaled on two of the protrusions. More specifically, since appropriately proportioned rings have inside surfaces slightly smaller than the unstressed or relaxed exterior diameter of the vessel ends and exterior diameters slightly larger than the relaxed exterior diameter of the vessel, there is seldom a problem in impaling the vessel on the first two of the protrusions, but tearing often occurs when stretching the vessel to impale it on the third. Thus, it is desirable to avoid vessel tearing during the impaling process to provide a stable, patent anastomosis.

One known solution to tearing of vessels is disclosed in U.S. Pat. No. 4,693,249, issued to Schenck et al., as an anastomosis ring which is shiftable between a contracted state and an expanded state. More specifically, as disclosed, the ring is contracted when the vessels are being interconnected and impaled on all of the protrusions and, then, is expanded to open more fully the vessel lumens for liquid flow therethrough.

It is a primary object of the present invention to provide a new and improved sutureless, extraluminary anastomosis device and method for interconnecting a first and second living vessel which reduces potential for tearing the vessels during the anastomosis procedure and assures patency at the anastomosis site.

It is another object of the present invention to provide such device and method in a manner which reduces the time consumption necessary for anastomosing ends of living vessels, which results in overall shortening of the surgical procedure.

An overall object of the present invention is to provide an anastomosis device which is efficient and cost effective to manufacture.

SUMMARY OF THE INVENTION

The present invention is directed toward a new and improved extraluminary anastomosis device for interconnecting a first living vessel with a second living vessel without interfering with liquid flow such as blood flow through the lumens of the vessels. The device comprises a single encircling member, or a ring-like body, of biologically compatible material through which an end of the first vessel extends and everts back over and an end of the second vessel extends over to engage the everted first vessel end. It further includes a plurality of fasteners spaced about the ring-like body for clinching the first and second living vessels to each other at the ring-like body.

The fasteners may comprise an elongated wire member with a split configuration, such as a staple-like configuration, to have a pair of legs and points on the ends of the legs. Initially, the points are spaced from one another a predetermined distance for allowing the fasteners to receive the vessel ends of the vessels without tearing the vessels. After being associated with the ring-like body and vessel ends, the fasteners are then shifted to their closed position in which the fastener points will impale the vessel ends to clinch the vessel ends, with their lumen in sealed opposition, at the ring-like body.

In the clinched, or closed position, each staple-like fastener has one leg located inside of the ring-like body, but exteriorly of the first living vessel and the other leg located exterior of the margin of the second living vessel at the ring-like body. The inner leg may be attached to the ring-like body.

The ring-like body may further include at least one needle-like projection for impaling the first and second vessel ends to hold them at the ring-like body. The projection may be designed to permanently secure the vessel ends at the ring-like body, or it may be shortened for temporarily holding the vessel ends at the ring-like body until the fasteners are inserted and clinched to permanently secure the vessel ends. For either of these purposes, the needle-like projection may extend from the ring-like body back toward and outward from the first living vessel.

The present invention is further directed toward a method of anastomosing a prepared first living vessel end to a prepared second living vessel end. The method includes providing a ring-like body of biologically compatible material having an interior surface and exterior surface. The first vessel end is then extended through ring body and then everted back over the exterior surface of the ring body. The second vessel end is then extended over the everted first vessel end to bring their intima into sealing engagement.

For securing the first vessel end to the second vessel end at the ring body, a plurality of flexible fasteners of biologically compatible material are provided in which each has a first fastener end and a second fastener end for impaling the first and second vessels.

The first and second vessel ends are positioned between the legs of the fastener with the fastener substantially encompassing the ring body and the vessel ends. Finally, each of the fasteners are closed to force the fastener ends towards one another to impale the vessel ends for securing the same at the ring body.

The method may further include the step of holding the ring body with a surgeon's tool for controlling the ring body during insertion of the fasteners. The tool may comprises a pair of opposing jaws which each may include a recess located at the jaw's distal end and where the recesses open away from one another. Each recess is complementarily adapted to engage the ring at diametrically opposed locations. The tool, via the recesses, grips the ring body and prevents rotational movement of the ring body relative to the tool. The tool may further include means for locking the jaws so to grip the ring body without manual force by the surgeon.

Alternatively, the recess of each jaw may be located on the jaw's interior to open towards one another. Hence, this alternative tool grips the ring body at a single location.

Additionally, the method may further include the step of controlling the first and second ends of the vessels with a surgeon's tool having a tool end adapted to impale and then hold the vessels for simultaneously everting the first vessel end over the exterior surface of the ring body and extending the second vessel end over the everted first vessel end for holding the vessel ends while inserting and closing the fasteners.

To close the fasteners at the ring-like body, a surgeon's tool may be employed. A preferred surgeon's tool may include a handle for holding and manipulating the tool, means for engaging the fastener at a plurality of locations and means for driving the engaging means to cause the legs of the fastener to be closed for clinching the first and second vessel ends in sealed apposition at the ring-like body. The engaging means may comprise a pair of opposing jaws capable of moving towards one another to cause the fasteners to shut. The driving means may comprise a collar slidably mounted on the jaws. The collar may be slid towards the fastener to cause the jaws to shut the fastener. Additionally, the tool may include a plurality of jaws grouped in pairs, each group having a collar for being able to close all the fasteners substantially simultaneously.

Alternatively, the driving means may be included in the handle which is squeezable by a surgeon's hand to close the jaws to shut the fastener. The driving means may also be a screw to move the jaws toward one another for holding the fastener and closing further to shut the fastener.

In an even further alternative embodiment, the surgeon's tool to clamp shut the fasteners may include an elongated fixed member having a handle at one end for being held by the surgeon. And coupled to the fixed member for linear travel relative to the fixed member is an elongated shiftable member capable of traveling to engage the fastener outside the margins of the vessels to drive the fastener against the engaging end of the fixed member to close the fastener. The coupling may include a linear dovetail formed from the shiftable member and a complementary dovetail groove formed in the handle for receiving the linear dovetail. The fasteners may include an aperture in the leg located between the ring-like body and the first vessel; and the engaging end of the fixed member may include a projection capable of being received in the aperture for locating the tool with the fastener and to prevent displacement of the tool relative to the fastener.

BRIEF DESCRIPTION OF THE DRAWINGS

The present invention will be described in connection with the accompanying drawings, which illustrate the preferred embodiments and details of the invention, and in which.

DETAILED DESCRIPTION OF THE PREFERRED EMBODIMENT

As shown in the drawings for purposes of illustration, the present invention provides an anastomosis device 10 (FIG. 6) for interconnecting a first living vessel 12 to a second living vessel 14. In general, the device 10 includes a ring-like body 22, or an encircling member, at which the proximal vessel end 16 and distal vessel end 18 of the first and second vessels 12 and 14, respectively, are associated at, and clinched to, with fasteners 20. More particularly, the proximal end 16 of the first vessel 12 is extended through and everted back over the ring body 22, and then, the distal end 18 of the second vessel 14 is drawn over the everted proximal vessel end 16. The fasteners 20 are next employed to impale the vessel ends 16 and 18 and secure them in sealed opposition at the ring body 22. This device has important advantages in that it can be employed to quickly anastomosis vessels, including relatively small vessels, such as 0.5 millimeter in diameter and smaller. Further, the device holds open the lumen of the vessel ends to aid in assuring that the anastomosis remains patent. Moreover, the ring body 22 and fasteners 20 are all "extraluminary" and therefore have no effect on blood flow which further aids in assuring potency at the anastomosis site.

Figure 3:
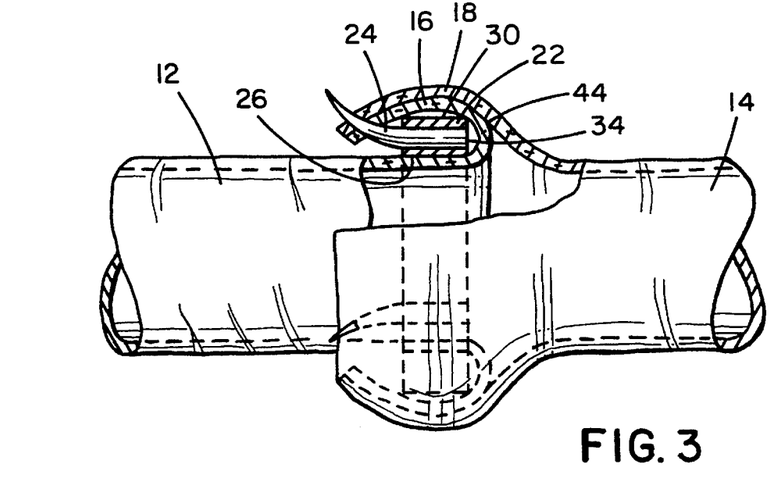
FIG. 3 is a partial cross-sectional side view of the ring-like body of FIG. 1 being employed to interconnect a pair of vessels.

In addition, the ring-like body 22 may include impaling protrusions 24 which extend parallel to the central axis of the body 22 initially and curve outward from such axis proceeding along the protrusions 24 away from the body 22. The protrusions 24 are designed to impale the vessel ends 16 and 18 for securement at the body 22 and may be used in combination with fasteners (FIG. 6), such as fasteners 20, or without any additional fasteners (FIG. 3). For example, the protrusions may be designed to only temporarily secure the vessel ends 16 and 18 until the fasteners 20 can be inserted and closed to more permanently clinch the vessel ends 16 and 18 at the ring-like body 22.

Altogether, the device 10, and method of employing the same, provide an effective sutureless anastomosis procedure which reduces the time necessary for anastomosing living vessels and assures patency at the anastomosis site.

Figure 1:
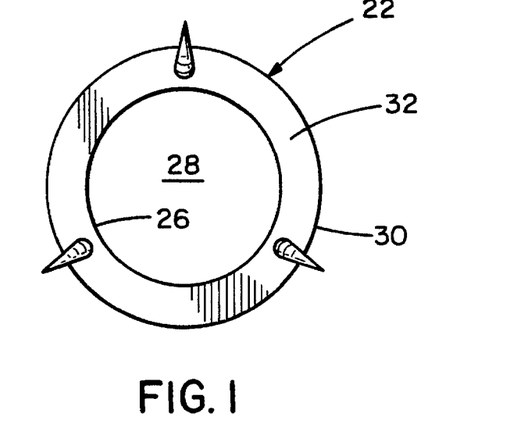
FIG. 1 is a front elevational view of a ring-like body of an anastomosis device of the present invention illustrating the use of needle-like projections to secure the vessels at the ring-like body.
Figure 2:
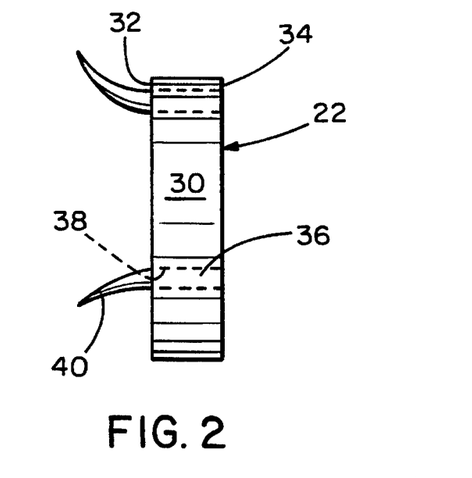
FIG. 2 is a side elevational view of the ring-like body of FIG. 1.

More particularly, the ring-like body 22 is made from a biologically compatible material. For instance, the ring body 22 may be cyclotron fabricated rings of metal, or they may be formed of a suitable absorbable organic composition, such as polyglycolic/polyactic acid. As illustrated in FIGS. 1 and 2, the body 22 forms a complete ring having an interior surface 26 defining a central opening 28, an exterior surface 30, a front surface 32 and a rear surface 34. One manner of making the ring bodies is to use a laser to cut very small and delicate rings from a sheet of plastic material.

It is found that such devices are most useful if their exterior diameter is slightly larger than the relaxed exterior diameter of the vessel ends being joined. This results in the anastomosed vessel ends being radially stressed outward along the exterior surface of the device. To accommodate the necessary radial thickness of the device, the interior diameter is equal to the natural, relaxed exterior diameter of the vessel ends. Therefore, the diameter of the vessel passageway maintained by the eversion of the first proximal vessel end around the ring-like body ensures patency at the anastomosis site. For instance, in the case of a vessel having a relaxed exterior diameter of approximately 1.0 millimeter, the body may have an outer diameter of approximately 1.2 millimeter and an inner diameter of approximately 1.0 millimeter.

The impaling protrusions 24 may be made from a similar biologically compatible material as that mentioned supra for the ring-like body or a metal such as that used to make surgical needle portions and preferably extend from the body 22 at generally evenly spaced circumferential locations. For instance, if the device 10 has three protrusions 24, as illustrated in FIG. 1, they are spaced approximately 120 degrees apart. Similarly, if there are four protrusions, they would be spaced approximately 90 degrees apart. The preferred protrusions are so small and so sharp that they are like a surgical needle or a portion of a surgical needle in their construction.

As shown in FIG. 2, each of the protrusions 24 includes a linear portion 36 for mounting it to the body 22 and an arcuate portion 40, or hook, for impaling and securing the vessel ends at the body 22. More specifically, the linear portion 36 is received in an aperture 38 formed in the body 22 from the front surface 32. This sets the linear portion 36 parallel to the central axis of the central opening 28 (FIG. 1). The diameter of the apertures 38 are such to admit the linear portion 36 with a fit not allowing the protrusion 24 to readily release out of the aperture 38. For instance, to accommodate a protrusion wherein its linear portion has a diameter of approximately 50 microns, the aperture would have a diameter of approximately 60 microns. This clearance allows the protrusion to be inserted with a snug fit. In addition, a bonding substance may be employed to further secure the protrusion in the aperture.

Proceeding outward from the front surface 32 of the body, each of the arcuate portions 40 curves outward from the body 22, as illustrated. This outward curvature, which is further aided by the contracting forces at the vessel ends 16 and 18, prevents the impaled vessel ends from becoming detached from the protrusions 24. At its free end, each of the arcuate portions 24 is configured to have a needle tip 42 to impale the vessel ends 16 and 18.

Figure 6:
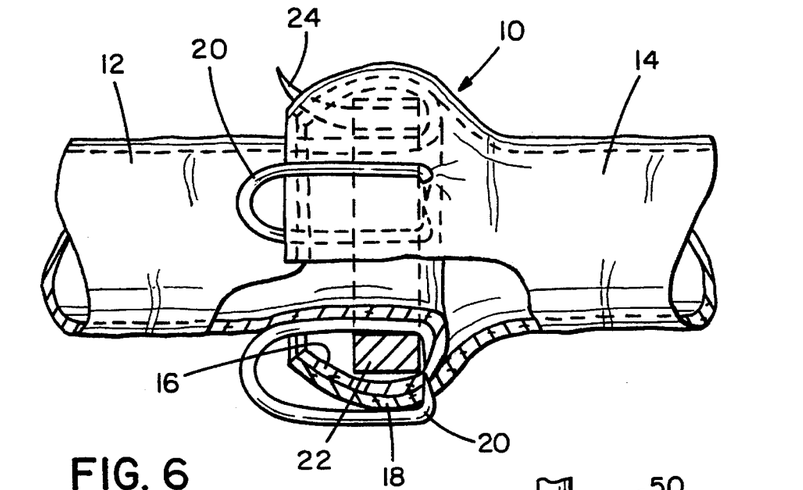
FIG. 6 is a partial cross-sectional side view of the ring-like body of FIG. 1 illustrating the use of staple-like fasteners of FIG. 4 for clinching the vessels at the ring-like body.

As indicated, the protrusions 24 may be designed to either temporarily (FIG. 6) or permanently (FIG. 3) secure the vessel ends 16 and 18 (i.e., to be used with or without additional fasteners). As illustrated in FIG. 6, the protrusions 24 are designed to temporarily hold the vessel ends until the fasteners 20 are set in place and clinched. More particularly, once the proximal vessel end 16 is extended through and everted back over the ring body 22, it is impaled on the impaling protrusions 24. Similarly, once the distal vessel end 18 is drawn over the everted proximal vessel end 16, it is also impaled on the impaling protrusions 24. This brings the intima 44 of the two vessel ends 16 and 18 into a sealing apposition. When the protrusions 24 are employed for temporarily securing the vessel ends 16 and 18, they may be shorter in length than if used for permanent securing of the vessel ends 16 and 18.

Figure 4:
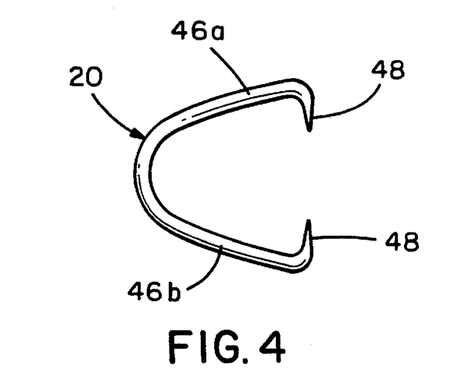
FIG. 4 is a side elevational view of a staple-like fastener of the anastomosis device of the present invention in its open, insertable state.
Figure 5:
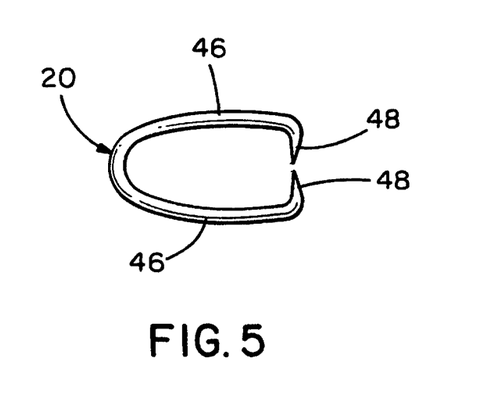
FIG. 5 is a side elevational view of the staple-like fastener of FIG. 4 in its closed, clinching state.

As best shown in FIG. 6, the fasteners 20 are positioned at predetermined locations, such as at evenly spaced circumferential locations about the ring body 22, for securing the vessel ends 16 and 18. As illustrated in FIGS. 4 and 5, each of the fasteners 20 has a staple-like configuration with a generally C-shaped body, as viewed in side elevation. Each fastener 20 is constructed from a biologically compatible, wire-like material to have a pair of legs 46, each terminating with a point 48, or needle, for impaling the vessel ends 16 and 18. These staple-like fasteners are extremely small and are much smaller in size than commonly used surgical staples that are commercially available.

More particularly, each fastener 20 is shiftable from an open position (FIG. 4) in which the points 48 are distanced sufficiently to receive the body 22, with the everted and drawn vessel ends 16 and 18, respectively, therebetween to position the fastener 20 and the ring body 22 and a closed position (FIG. 5) in which the points 48 have been moved substantially closer to one another to first impale and then clinch the vessel ends 16 and 18 together at the body 22. This clinching brings the intima 44 of the two vessel ends 16 and 18 into sealing apposition (FIG. 6).

In the open position, the fastener points 48 are preferably set apart so not to tear the vessel ends 16 and 18 when being associated with the same. The fasteners may be pre-fabricated with the points suitably spaced or this may be manually done by the surgeon. Each of the fasteners 24 are associated from the front side of the ring body 22 (i.e., the side from which the proximal vessel end 16 extends through the body 22). For each of the fasteners, one of the legs 46a travels between the ring body 22 and the first vessel 12, while its point 48 crosses over the interior surface 26 of the ring body 22 until it passes through the body 22 itself, and the other leg 46b passes over the exterior surface of the second vessel end 18 with sufficient clearance so that its point 48 does not tear or otherwise damage the vessels 12 and 14. Once the points 48 have traveled across the ring body 22, the fastener 24 is closed to clinch the vessel ends 16 and 18 in a sealed apposition at the ring body 22.

Figure 7:
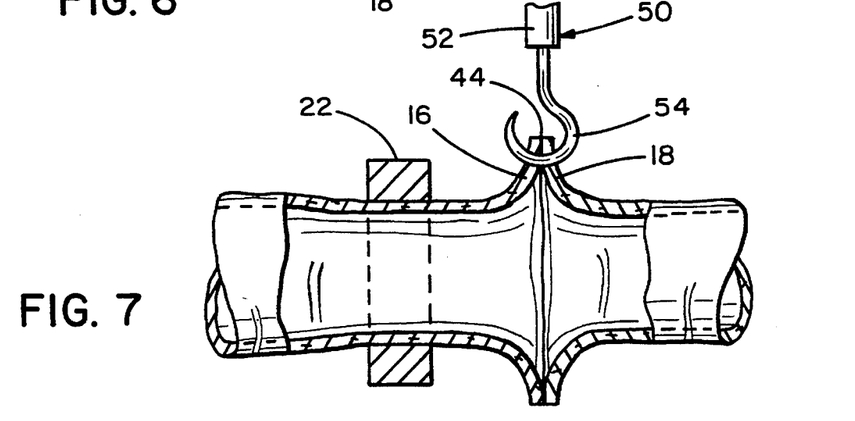
FIG. 7 is a partial cross-sectional side view of a ring-like body in accordance with the present invention illustrating the use of a surgeon's tool for simultaneously associating the vessels with the ring-like body.
Figure 8:
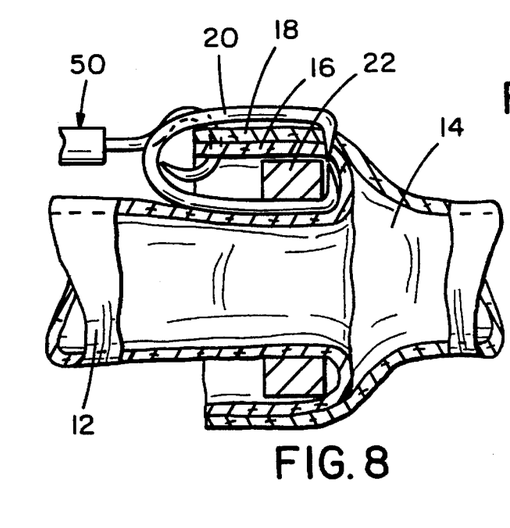
FIG. 8 is a partial cross-sectional side view of the ring-like body of FIG. 7 further illustrating the use of the staple-like fastener of FIG. 4 in combination with the surgeon's tool of FIG. 7.

As illustrated in FIGS. 7 and 8, a surgeon's hook-like tool 50 may be used to simultaneously evert the proximal vessel end 16 and draw the distal vessel end 18 over the everted proximal vessel end 16 and the body 22. The tool 50 includes a handle 52, or shaft, for being held and easily manipulated by a surgeon's hand and a hook 54 located at the opposite end for impaling and holding the vessel ends 16 and 18. In using the tool 50, the proximal vessel end 18 is inserted through the body 22, and then both vessel ends 16 and 18 are impaled on the hook 54 of the tool 50 with their intima 44 in apposition.

With the ring body 22 parked distally of the hooked vessel ends 16 and 18, the tool 50 is drawn back toward the ring body 22 to evert the proximal vessel end 16 over the body 22 and to simultaneously draw the distal vessel end 18 over the everted proximal vessel end 16 and to hold the vessel ends 16 and 18 in this position and then the fasteners 20 are closed to clinch the vessel ends 16 and 18 together at the body 22. It is also in accordance with the present invention that the tool 50 may be employed to position the vessel ends 16 and 18 and impale them on the protrusions 24 for either permanent (FIG. 3) or temporary securement (FIG. 6). The illustrated fasteners 20 may be finished separately or they may have their inner leg secured to the inner wall of the ring. By securing the lower leg to the ring, it also is necessary to close the staple outer leg without having to manipulate the fastener into position onto the ring before one can close the staple.

The degree of stretching which a vessel end can withstand depends on the type and nature of the vessel. The most common use of the device described herein is for anastomosing blood vessels. However, the device may be used equally as effective with other living vessels, such as fallopian tubes, vas deferens, nerve sheaths, ureters, etc. Furthermore, even vessels for the same general purpose, e.g., different blood vessels, may have substantially different tear strengths and elasticity, depending, for example, on the amount of muscle tissue surrounding the vessels. Devices according to the present invention are most advantageous for joining vessels that are most susceptible to tearing; however, advantages for even stronger vessels can be appreciated, such as allowing the use of larger devices that provide a larger vessel passageway after anastomosis.

In order to further accommodate a larger number of vessel types, the device may include a shiftable, split ring-like body 60 which has a smaller size (FIG. 9A), or contracted state, when the blood vessels are being associated with the ring, as described infra, and, then, the body 60 has a larger size (9B), or expanded state, to open more fully the vessel lumens for fluid flow therethrough. The illustrated and preferred ring-like bodies are biased to one state, either the expanded or contracted state, and the surgeon shifts them to their other state, either expanded or contracted.

Figure 9A:
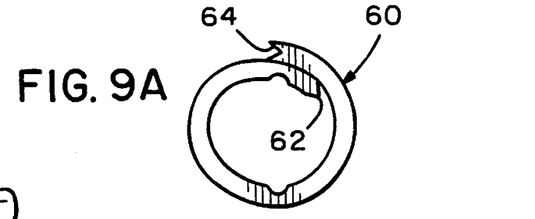
FIG. 9A is a front elevational view of an alternative ring-like body, having a split configuration shown in its contracted state, of an anastomosis device for interconnecting living vessels in accordance with the present invention.
Figure 9B:
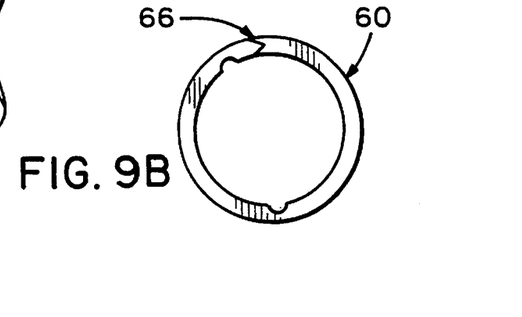
FIG. 9B is a front elevational view of the alternative ring-like body of FIG. 9A shown in its expanded state.

For instance, the ring-like body 60, as shown in FIG. 9A, is biased to its smaller diameter, contracted state, prior to having the blood vessels associated therewith, and the surgeon will expand the ring and bring its ends 62 and 64 into locking engagement 66 to hold the ring-like body 60 in its expanded state. After the vessel ends have been placed in a sealed apposition as described supra at the ring-like body 60. Suitable split ring-like bodies, and methods of shifting the same, are disclosed in U.S. Pat. No. 4,693,249, issued to Schenck et al. on Sep. 15, 1987, which is incorporated herein by reference.

Figure 10:
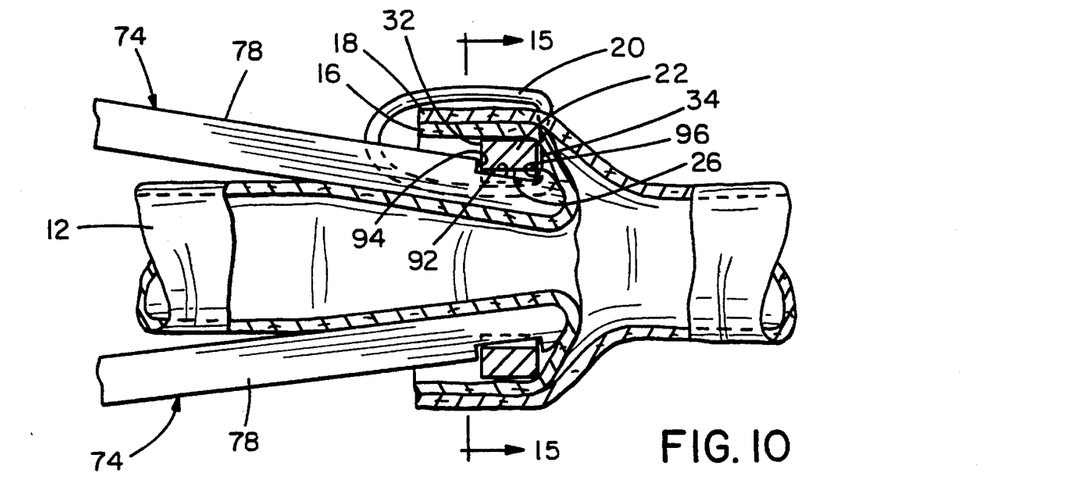
FIG. 10 is a partial cross-sectional view of the anastomosis device of the present invention illustrating the use of a surgeon's tool for controlling the ring-like body of FIG. 7 while installing the anastomosis device.
Figure 11:
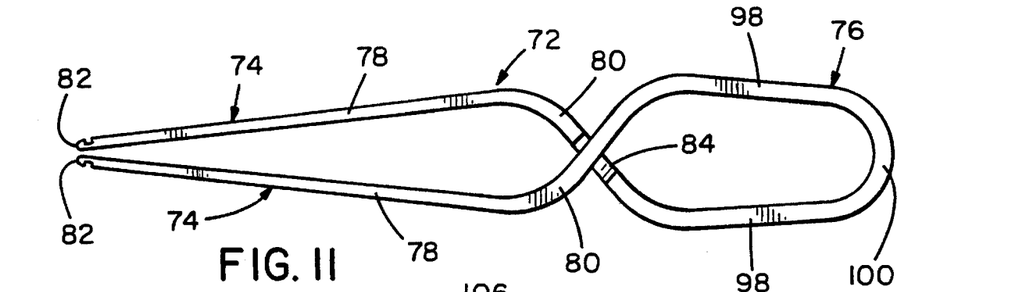
FIG. 11 is a side elevational view of the surgeon's tool illustrated in FIG. 10.
Figure 15:
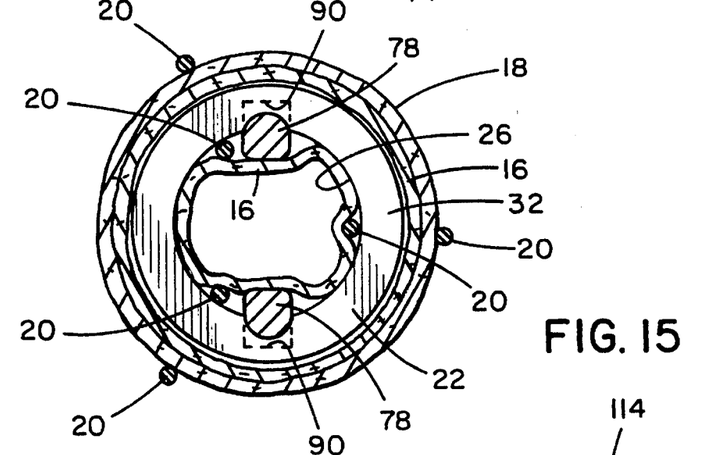
FIG. 15 is a cross-sectional view taken along line 15—15 of FIG. 10.

As illustrated in FIGS. 10, 11 and 15, the body 22 may be held and controlled by a surgeon's tool 72 while the fasteners 20 are inserted and closed to clinch the vessel ends 16 and 18 at the body 22. More particularly, the tool 72 may be the type of a reverse action bayonet which includes a pair of opposing forcep jaws 74, or legs which remain closed when no force is applied to a handle portion 76. The jaws 74 cross and extend continuously to form a handle portion 76. Each of the jaws 74 includes a linear portion 78 and an inward arcuate portion 80 stemming to the handle portion 76.

More particularly, when the tool 72 is not being used, as illustrated in FIG. 11, the jaws 74 are biased to a closed position in which the opposing free ends 82 are substantially proximal to one another and the linear portions 78 slope away from one another proceeding towards the arcuate portions 80. The linear portions 78 are of suitable length to reach in along and between the first vessel 12 and the body 22 for grasping the interior surface 26, as illustrated in FIG. 10.

The arcuate portions 80 curve back towards one another to cross. At this intersection, one of the arcuate portions 80, or possibly both, is formed with an outward bend 84, or recess, so that the two cross in substantially the same plane.

Figure 13:
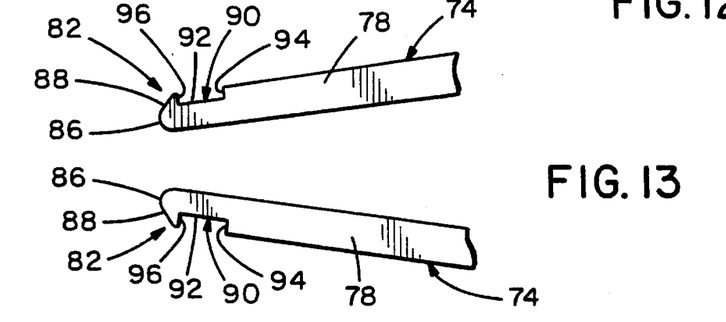
FIG. 13 is enlarged partial elevational view of the ends of the surgeon's tool illustrated in FIGS. 11 and 12 depicting a pair of recesses for gripping the ring-like body as illustrated in FIG. 10.

As best illustrated in FIGS. 10 and 13, the outer free end 82 of each linear portion 78 is configured with an arcuate surface 86 to round off the end for inserting it between the body 22 and the first vessel 12 without tearing, or otherwise damaging, the same. Further, each end 82 is formed with a linear camming surface 88 which cams against the interior surface 26 of the body 22 and cooperates with the arcuate surface 86 to pry back the first vessel 12 from the body 22 to set a pair of recesses 90, which are each located adjacent one of the free ends 82, to receive the ring body 22.

Each recess 90 opens outward relative to the other for engaging the body 22 at diametrically opposed locations. The recesses 90 are complementarily adapted with the body 22 to receive it therein for control. That is, each recess 90 is formed with approximately 90 degree cuts relative to the jaw 74 and is defined by a bottom surface 92 and a pair of side surfaces 94 and 96, and wherein these surfaces engage the inner, front and back surfaces 26, 32 and 34, respectively, of the body 22. This engagement prevents rotational movement of the body 22 relative to the tool 72 and prevents the ring body 22 from slipping off the jaws 74. Thus, the body 22 is easily and reliably controlled by the surgeon during the anastomosing procedures.

The handle 76 is suitably sized for being gripped by one hand of a surgeon and for being squeezed by the hand for forcing the jaws 74 apart in order to apply the recesses 90 to the body 22, as illustrated in FIG. 10. As best illustrated in FIG. 11, the handle 76 includes a pair of linear portions 98, which are gripped and squeezed by the hand, and an arcuate end portion 100 which biases the jaws 74 toward the above-described closed position.

When great manual force is applied, the jaws 74 may be used to expand an expandable ring body, such as the above-described split ring-like body 60. However, the necessary force tends to make the tool 72 difficult to control manually.

Figure 12:
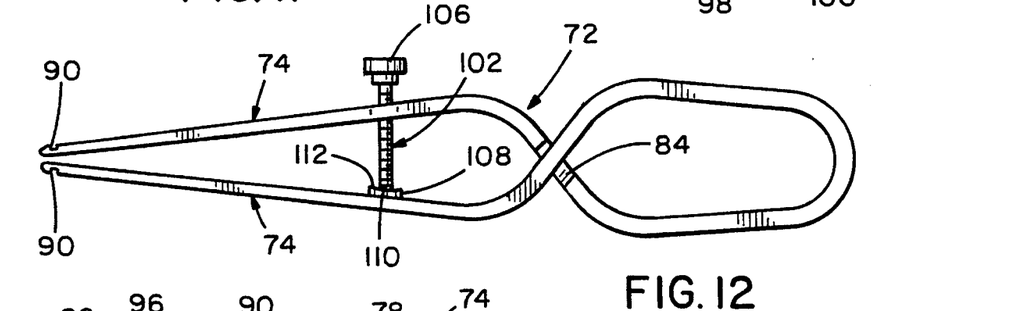
FIG. 12 is a side elevational view of an alternative embodiment of the surgeon's tool illustrated in FIG. 11.
Figure 14:
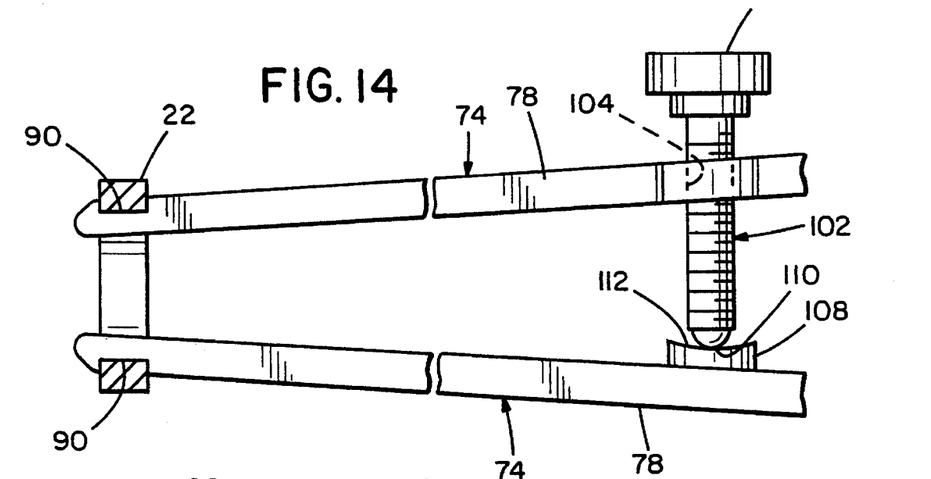
FIG. 14 is an enlarged partial elevational view of the surgeon's tool of FIG. 12 for gripping the ring-like body illustrating a drive mechanism for its operation.

Preferably, as illustrated in FIGS. 12 and 14, the tool 72 may include a threaded bolt or screw 102 for applying force to move the jaws 74 for engaging the recesses 90 with the body 22. More particularly, the screw 102 enables the jaws 74 to be opened easily, slowly and in a controlled fashion. The screw 102 may be a threaded screw set in a threaded hole 104 in the linear portion 78 of one of the jaws 74. The screw 102 includes a turning knob 106 at one end for turning the screw 102, and at its opposite end, the screw 102 abuts a plate 108 mounted internally on the opposing linear portion 78 of the other jaw 74. The internal plate 108 allows the screw end 110 to slide as the jaws 74 open and close and may include a concave surface 112 which guides the screw end 110 in a definite controlled manner while it slides thereover. The screw 102 enables finite, diminutive adjustments to be made and relieves the surgeon from having to maintain constant pressure with the hand to engage the recesses 90 with the body 22.

Figure 16:
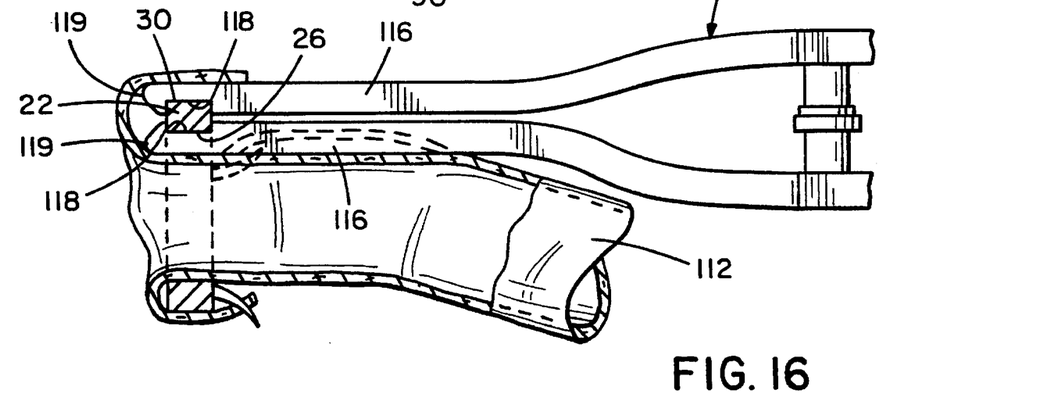
FIG. 16 is a partial elevational view of another alternative surgeon's tool being employed to control the ring-like body of FIG. 1 while installing the anastomosis device of the present invention.

As illustrated in FIG. 16, an alternative surgeon's tool 114, similar to a castroviejo needle holder, may be used to grip the body 22 at a single location to securely hold the body 22 to prevent rotational movement. This alternative tool 114 includes a pair of linear portions 116, or forceps, with each having a recess 118 located proximally to the distal free end. The forcep free ends 119 and the recesses 118 are identical to the free ends 82 and recesses 90 for the tool 72 described supra with the exception that they are reversed for allowing the recesses 118 to open towards one another for grabbing the body 22 at a single location. That is, the tool 114 grips the body 22 at the interior surface 26 with one of the recesses 118 and the exterior surface 30 with the other recess 118 at the same location on the body 22. The tool 114 may also include a locking mechanism, such as a castroviejo type locking mechanism, which locks the forceps into engagement with the ring body 22 without any manual work exerted by the surgeon.

Figure 17:
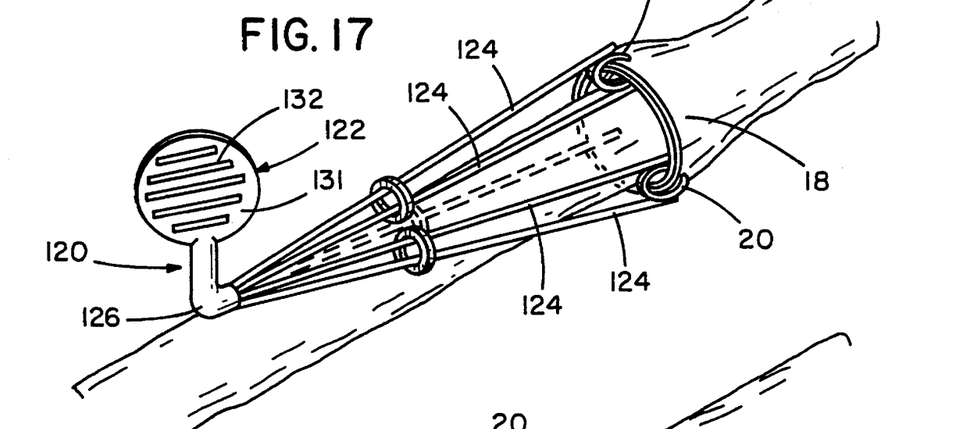
FIG. 17 is a perspective view of a surgeon's tool for closing fasteners in accordance with the present invention.

After the fasteners 20 have been properly associated with the ring body 22, a tool 120, or closing device, may be employed to shift each of the fasteners 20 from their open position to their closed position for clinching the vessel ends 16 and 18 at the ring body 22, as illustrated in FIG. 17. It is preferred that the tool 120 include means for closing each of the fasteners separately and simultaneously, or at least substantially simultaneously. For instance, if three fasteners 20 are used, it is preferred that the tool 120 be able to engage and shift all three of the fasteners, as illustrated.

More particularly, the tool 120 includes a handle 122, or grasping portion, for handling and controlling the tool 120 itself, and a number of arms 124, or rods, for closing the fasteners 20. The handle 122 may be configured as a tab with front and back surfaces 131, each surface 131 having horizontal gripping ribs 132. The handle 122, or tab, can be held by a surgeon's fingers or by another surgeon's tool, such as self-locking forceps, which in turn may be held by the surgeon.

The handle 122 is connected to the arms 124 by an L-shaped elbow member 126. All the arms 124, or rods, extend angularly outward and away from the elbow member 122 for being capable of engaging all the fasteners 20 simultaneously. The arms 124 are paired in groups of two so that each group is capable of working one of the fasteners 20 at diametrically opposed locations.

Figures 18, 19:
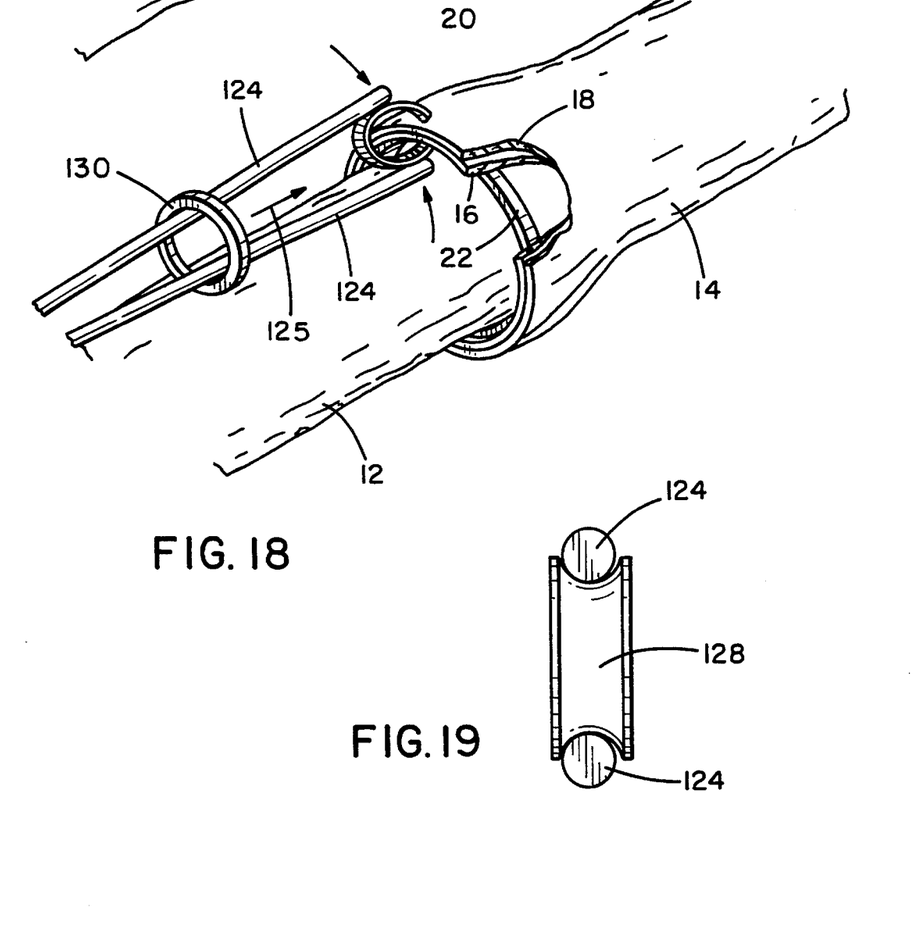
FIG. 18 is an enlarged partial perspective view of the surgeon's tool of FIG. 17 being employed to close a fastener with a partial sectional view at the ring-like body.
FIG. 19 is an enlarged side elevational view of an alternative fastener embodiment of the present invention being closed by the surgeon's tool of FIG. 17.

As illustrated best in FIG. 19, each of the fasteners 20 may be configured with an inwardly concave, annular recess 128 for complementarily receiving the arms 124 of one group. The recess 128 prevents the arms 124 from displacement relative to the fastener 20 when force is exerted upon the arms to hold or to shift, i.e., squeeze, the fastener 20 to the closed position.

As illustrated in FIGS. 18 and 19, to force the arms 124 together for closing the fasteners 20, a slidable C-ring 130, or collar, is provided for each pair of arms 124. The arms 124 are flexible, and as the ring 130 slides on the arms 124 towards the fastener 20, as indicated by the arrow having reference numeral 125, it pinches the fastener 20 to its closed position. It is also desirable that all the C-rings be moved simultaneously, or at least substantially simultaneously, to reduce the anastomosing procedure time.

For example, if three fasteners 20 are employed to clinch the vessel ends 16 and 18 to the ring body 22, it is desirable that the tool 120 include three sets of flexible arms 124 with each having a slidable C-ring 130. Thus, in closing all three fasteners 20, it is preferred that the surgeon slide the three rings 130 simultaneously, or substantially simultaneously, towards their respective fastener 20. This aids in reducing the overall surgical anastomosing procedure time, which in turn increases the effectiveness of the anastomosis.

Figure 20:
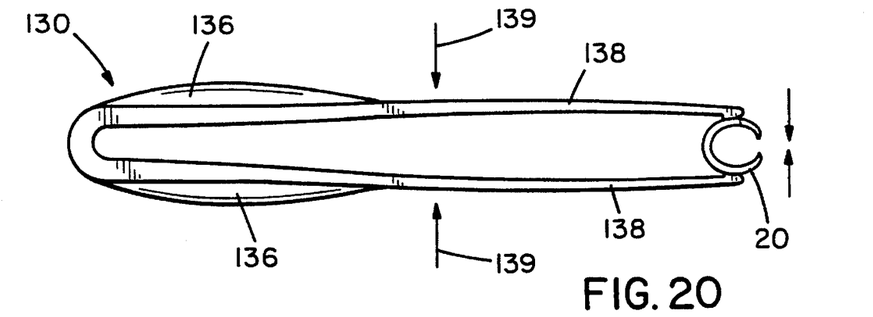
FIG. 20 is a side elevational view of an alternative surgeon's tool for closing fasteners in accordance with the present invention.
Figure 21:
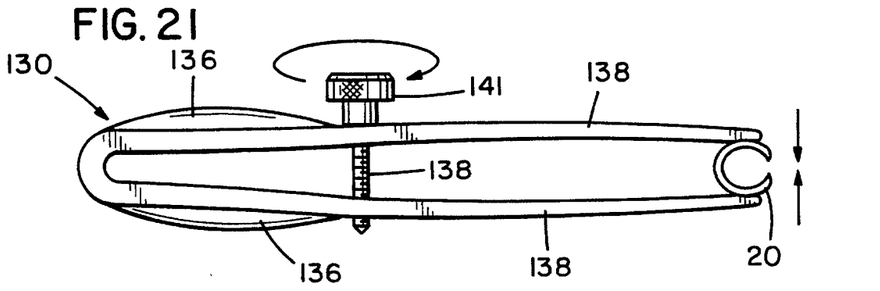
FIG. 21 is a side elevational view of the surgeon's tool of FIG. 20 adapted with a drive mechanism for operating the tool.

Alternatively, as illustrated in FIG. 20, each of the staple-like fasteners could be held by a forceps tool 130 having a handle 136 and a pair of outwardly biased opposing arms 138 for engaging the fastener 20. The handle 136 is adapted to be held by a surgeon in one hand so that, when the handle 136 is squeezed by one surgeon, it causes the arms 138 to close, as indicated by the arrow having reference manual 139, to shut the fastener 20, thereby clinching the vessel ends in sealed apposition at the ring-like body. Even further, as illustrated in FIG. 21, the forceps could be provided with a screw set 140 having a turning knob 141 which could be turned to bring the forcep arms 138 together to hold and then turned further to close the fastener 20. The 138 screw is threaded across the pair of biased opposing arms 138, and when turned counters the bias to close the arms 138.

Figure 22:
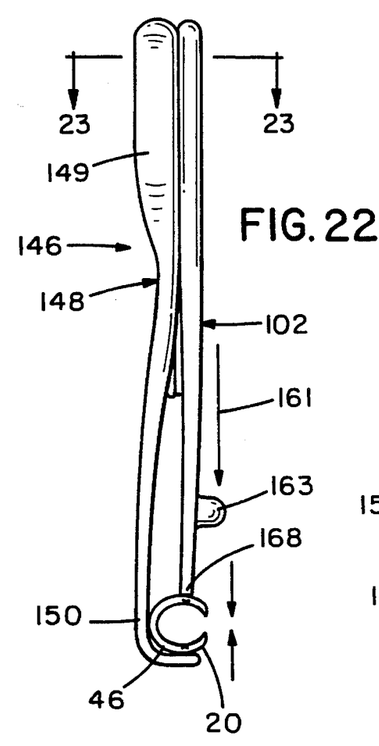
FIG. 22 is a side elevational view of an alternative surgeon's tool for closing fasteners in accordance with the present invention.
Figure 23:
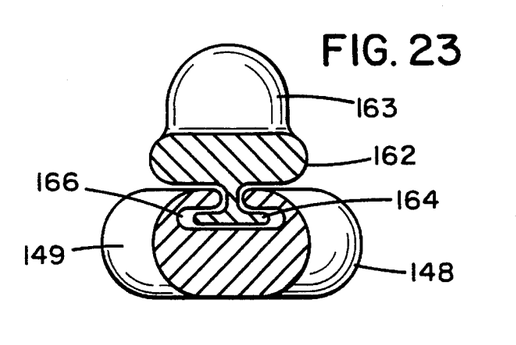
FIG. 23 is a cross-sectional view of the surgeon's tool of FIG. 22 taken along line 23—23 of FIG. 22.
Figure 24:
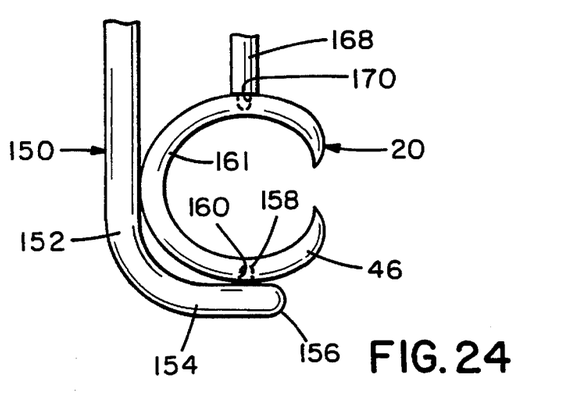
FIG. 24 is a enlarged elevational view showing a portion of the surgeon's tool of FIG. 22 to illustrate its engagement with a fastener in accordance with the present invention.

In an even further embodiment, as illustrated in FIGS. 22–24, there is closure tool 146 which is designed to approach the fastener 20 substantially normal to the vessel ends. The tool 146 comprises a handle member 148, or fixed member, which becomes temporarily affixed (FIG. 24) to the arm 46 of the fastener 20 located inside the ring body 22.

More specifically, the handle member 148 includes a lower L-shaped fastener closing end portion 150 having a vertical arm 152 and a horizontal arm 154. The horizontal arm 154 has a rounded end 156 configured to slip in between the fastener 20 and the first vessel without damaging the vessel and, also, includes a small projection 158. The projection 158 is received in a similarly sized aperture 160 formed in the inner arm 46 of the fastener 20 (FIG. 24).

The projection 158 aids in locating the tool 146 with the fastener 20 for effective closing of the fastener 20. That is, in the preferred embodiment, the aperture is located equidistantly from the end of the fastener arm 46 and the curved portion 161 interconnecting the other fastener arm 46 to give advantageous leverage. The engagement between the projection 158 and fastener 20 also prevents displacement between the fastener 20 and the tool 146 which could damage the vessels.

The vertical arm 152 connects the horizontal arm 154 to the handle member 148. When closing a fastener 20 with the tool 146, the vertical arm 152 may engage the curved portion 161 of the fastener 20, as illustrated in FIG. 24.

To close the fastener 20, the tool 146 includes a moveable driver member 162, or shiftable member, which moves with respect to the handle member 148. The driver member 162 has a driver end 168 to engage and drive the fastener 20 to its closed position. The fastener 20 may also include an aperture 170 which the driver end 168 to further prevent displacement of the tool 146 relative to the fastener 20.

The driver member 162 is coupled to the handle member 148 for linear travel. The drive member 162 includes a linear dovetail 164 having a substantially T-shaped cross-section which is received in a cooperating linear dovetail groove 166 formed in the handle portion 148. More specifically, the handle portion 148 is formed to have a substantially T-shaped cross-section which forms the groove 166. This cooperating engagement between the handle member 148 and the moveable driver member 162 allows the latter to slide and reciprocate rectilinearly and prevent substantial lateral movement of the driver member 162.

The mounting portion 164 slides in the groove 166 toward the fastener 20 as indicated in FIG. 22 by the arrow having reference manual 161, to engage the driver end 168 for pinching the fastener between itself and the horizontal arm 154 to driver the fastener 20 to its closed portion. For holding the fixed member 148, it has a widened upper end 149 for being easily held in a surgeon's hand, and for moving the slidable member 162, it is provided with a knob 163, which may be located anywhere along the slidable member 163 at a position which easily facilities movement thereof but does not allow the surgeon's hand to interfere with the closing of the staple 20.

From the foregoing, it is seen that the objects hereinbefore set forth may readily and efficiently be attained, and since certain changes may be made in the above construction and methods and different embodiments of the invention without departing from the scope thereof, it is intended that all matter contained in the above description or shown in the accompanying drawings shall be interpreted as illustrative and not in a limiting sense.

What is claimed is:

1. An apparatus for anastomosing a prepared first living vessel end to a prepared second living vessel end comprising:

an encircling member having an interior surface and an exterior surface and through which the first vessel end of the first living vessel extends to pass the interior surface to evert over the exterior surface and the second end of the second living vessel extends over the encircling member to engage the everted first vessel end of the first living vessel to interconnect the living vessels in apposition at the encircling ring; and at least one needle-like projection extending from the encircling member back toward the first living vessel as the vessel extends through the encircling member for holding the first and second vessel ends in a sealed apposition at the encircling member;

the encircling member further comprising a plurality of fasteners having each an elongated wire-like body with a substantially enclosing configuration, a pair of opposing ends for impaling the vessels and flexibility to change from a first position in which the ends are spaced for enabling the fastener to be moveable by the surgeon to substantially encompass the encircling member and the vessel ends and a second position in which the ends impale the vessels adjacent the vessel ends while the fastener secures the vessel ends against the encircling member for securing the vessels in a sealed apposition at the encircling member.

2. An apparatus in accordance with claim 1 in which the fasteners are positioned at predetermined locations about the encircling member for effective binding of the vessels.

3. A method of anastomosing a prepared first living vessel end having a vessel wall to a prepared second living vessel end having a vessel wall comprising:

providing an encircling member of biologically compatible material in the form of a ring having an interior surface and an exterior surface;

extending the first vessel end through the encircling member, everting the first vessel end over the exterior surface, and then drawing the second vessel end over the everted first vessel end to bring their intima into apposition;

providing a plurality of flexible staple-like fasteners of biologically compatible material for securing the first vessel end to the second vessel end at the encircling member having each a first inner fastener leg and end and a second outer fastener leg and end for impaling the first and second vessels, the legs and ends thereof each being spaced apart at least a first predetermined distance;

positioning the first and second vessel ends over the ring member and between the ring member and the outer legs;

closing each of the fasteners by forcing the inner and outer legs relative to one another to impale the first and second vessel walls and to clamp the vessel walls in a sealed apposition at the encircling member; and including the step of controlling the first and second ends of the vessels with a surgeon's tool having a tool end to impale and then hold thereon the tool end the vessels for simultaneously everting the first vessel end over the exterior surface of the encircling member and the first vessel over the everted first vessel end simultaneously and for holding the vessel ends while inserting and closing the fasteners.

4. A method in accordance with claim 3 further comprising the step of hooking the first and second vessels with a surgeon's tool by impaling the first and second vessels adjacent to their vessel ends with the tool to force the vessel ends together as they are pulled over the exterior of the ring.

5. A method of anastomosing a prepared first living vessel end having a vessel wall to a prepared second living vessel end having a vessel wall comprising:

providing an encircling member of biologically compatible material in the form of a ring having an interior surface and an exterior surface;

extending the first vessel end through the encircling member, everting the first vessel end over the exterior surface, and then drawing the second vessel end over the everted first vessel end to bring their intima into apposition;

providing a plurality of flexible staple-like fasteners of biologically compatible material for securing the first vessel end to the second vessel end at the encircling member having each a first inner fastener leg and end and a second outer fastener leg and end for impaling the first and second vessels, the legs and ends thereof each being spaced apart at least a first predetermined distance;

positioning the first and second vessel ends over the ring member and between the ring member and the outer legs; and closing each of the fasteners by forcing the inner and outer legs relative to one another to impale the first and second vessel walls and to clamp the vessel walls in a sealed apposition at the encircling member; and the encircling member further comprising at least one projection extending therefrom and including the step of temporarily impaling the ends of the first and second living vessels with the projection to maintain the same at the encircling member while the fasteners are employed for securing the vessel walls in sealed apposition at the encircling member.

6. A method in accordance with claim 5 wherein the at least one projection extends back toward the first living vessel while curving outward from the first living vessel,

* * * * *

UNITED STATES PATENT AND TRADEMARK OFFICE
CERTIFICATE OF CORRECTION

PATENT NO. : 5,486,187

DATED : January 23, 1996

INVENTOR(S) : Robert R. Schenck

It is certified that error appears in the above-indentified patent and that said Letters Patent is hereby corrected as shown below:

Title page,

IN THE ABSTRACT:

Item [57] entitled "Abstract", page 1, line 17, after the word "fastener" change "are" to read --is--.

Column 13, line 8, (Claim 1, line 11), after the word "ring" delete "and".

Column 13, line 13, (Claim 1, line 16), after the word "member;" insert --and--.

Column 14, line 3, (Claim 3, line 28), change "thereon" to read --on--.

Column 14, line 31, (Claim 5, line 15), after the word "end" insert a comma --,--.

UNITED STATES PATENT AND TRADEMARK OFFICE
CERTIFICATE OF CORRECTION

PATENT NO. : 5,486,187
DATED : January 23, 1996
INVENTOR(S) : Robert R. Schenck

It is certified that error appears in the above-indentified patent and that said Letters Patent is hereby corrected as shown below:

Column 14, line 53, (Claim 6, line 3), after the word "vessel" change the comma "," to a period --.--.

Signed and Sealed this

Thirtieth Day of July, 1996

Attest:

BRUCE LEHMAN

*Attesting Officer*    Commissioner of Patents and Trademarks